United States Patent
Nakazawa et al.

(10) Patent No.: US 10,211,412 B2
(45) Date of Patent: Feb. 19, 2019

(54) CHARGE-TRANSPORTING VARNISH, CHARGE-TRANSPORTING THIN FILM AND METHOD FOR MANUFACTURING SAME, AND ORGANIC ELECTROLUMINESCENT ELEMENT AND METHOD FOR MANUFACTURING SAME

(71) Applicant: NISSAN CHEMICAL INDUSTRIES, LTD., Tokyo (JP)

(72) Inventors: Taichi Nakazawa, Funabashi (JP); Shoji Moriyama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 140 days.

(21) Appl. No.: 15/324,563

(22) PCT Filed: Jul. 9, 2015

(86) PCT No.: PCT/JP2015/069787
§ 371 (c)(1),
(2) Date: Jan. 6, 2017

(87) PCT Pub. No.: WO2016/006662
PCT Pub. Date: Jan. 14, 2016

(65) Prior Publication Data
US 2017/0155060 A1    Jun. 1, 2017

(30) Foreign Application Priority Data
Jul. 9, 2014  (JP) .................................. 2014-141348

(51) Int. Cl.
H01L 51/50        (2006.01)
H01L 51/00        (2006.01)
H05B 33/10        (2006.01)
C07D 487/04       (2006.01)
C09D 5/24         (2006.01)

(52) U.S. Cl.
CPC ........ H01L 51/0072 (2013.01); C07D 487/04 (2013.01); C09D 5/24 (2013.01);
(Continued)

(58) Field of Classification Search
None
See application file for complete search history.

(56) References Cited

U.S. PATENT DOCUMENTS

2014/0008624 A1    1/2014  Niina et al.
2014/0008626 A1    1/2014  Hayashida et al.
(Continued)

FOREIGN PATENT DOCUMENTS

CN    103814091 A       5/2014
EP    0 906 947    *   4/1999  ............ C09K 11/06
(Continued)

OTHER PUBLICATIONS

Nair et al., An Efficient synthesis of indolo[3,2-a]carbazoles via the novel acid catalyzed reaction of indoles and diaryl-1,2-diones, 2008, Org. Biomol. Chem., 6, 1738-1742 (Year: 2008).*
(Continued)

*Primary Examiner* — Gregory D Clark
(74) *Attorney, Agent, or Firm* — Birch, Stewart, Kolasch & Birch, LLP

(57) ABSTRACT

The invention provides a charge-transporting varnish, containing a charge-transporting substance formed of an indo-
(Continued)

locarbazole represented by the following formula (1), a dopant substance, and an organic solvent.

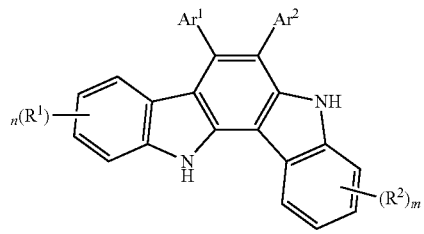

(1)

7 Claims, 3 Drawing Sheets

(52) U.S. Cl.
CPC .......... *H01L 51/0052* (2013.01); *H01L 51/50* (2013.01); *H05B 33/10* (2013.01); *H01L 51/0007* (2013.01); *H01L 51/5056* (2013.01); *H01L 51/5088* (2013.01)

(56) References Cited

U.S. PATENT DOCUMENTS

2014/0084279 A1 3/2014 Tanaka et al.
2014/0227815 A1 8/2014 Nakaie et al.

FOREIGN PATENT DOCUMENTS

WO WO 2012/132501 A1 10/2012
WO WO 2012/132556 A1 10/2012
WO WO 2013/002053 A1 1/2013

OTHER PUBLICATIONS

International Search Report for PCT/JP2015/069787 (PCT/ISA/210) dated Sep. 15, 2015.
Office Action dated Feb. 11, 2018, in Chinese Patent Application No. 201580037561.1.
Wang et al., "Theoretical Study on the Carrier Transport Properties of Indolo[3'2-b]carbazole Derivatives," Chemical Journal of Chinese Universities (2013), vol. 34, No. 6, pp. 1490-1496, with English abstract.

* cited by examiner (a)

(b)

CHARGE-TRANSPORTING VARNISH, CHARGE-TRANSPORTING THIN FILM AND METHOD FOR MANUFACTURING SAME, AND ORGANIC ELECTROLUMINESCENT ELEMENT AND METHOD FOR MANUFACTURING SAME

TECHNICAL FIELD

The present invention relates to a charge-transporting varnish, to a charge-transporting thin film, to a method for producing the same, to an organic electroluminescent element, and to a method for producing the element.

BACKGROUND ART

Hitherto, organic electroluminescent (hereinafter abbreviated as "organic EL") elements are known as light-emitting devices. Generally, organic EL elements have a multilayer structure including a positive electrode, a negative electrode, and charge injection layers (i.e., a hole injection layer and an electron injection layer) and a light-emitting layer, which intervene between the positive electrode and the negative electrode. In operation, injected electrons recombine with holes in the light-emitting layer, to thereby emit light.

In such a light-emitting layer and a charge injection layer, a charge-transporting thin film formed of an organic compound is employed. In particular, a hole injection layer disposed between the positive electrode and the light-emitting layer is involved in charge transfer to/from the positive electrode and the light-emitting layer, and thus plays an important role in attaining low driving voltage and high luminance of an organic EL element. Accordingly, various studies are now conducted on the material of a charge-transporting thin film for use in an organic EL element, in order to enhance characteristics of the organic EL element.

Meanwhile, the method of forming a charge-transporting thin film generally includes a dry process (typically, vacuum vapor deposition) and a wet process (typically, spin coating). Of these, a wet process is more advantageous, in that a large-area thin film with high flatness can be effectively formed.

Under such circumstances, there has been proposed a charge-transporting compound having a structure in which the two nitrogen atoms forming the indolocarbazole ring are substituted with an arylene group or a heteroarylene group (see, for example, Patent Document 1). There has also been proposed a charge-transporting compound having a structure in which the two nitrogen atoms forming the indolocarbazole ring are substituted with a polymerizable group (see, for example, Patent Document 2). There has also been proposed a charge-transporting compound having a structure in which the two nitrogen atoms forming the indolocarbazole ring are directly bonded to a main chain (see, for example, Patent Document 3). Some documents disclose synthesis of indolocarbazole compounds (see, for example, Non-Patent Document 1).

PRIOR ART DOCUMENTS

Patent Documents

Patent Document 1: WO 2013/002053, pamphlet
Patent Document 2: WO 2012/132501, pamphlet
Patent Document 3: WO 2012/132556, pamphlet

Non-Patent Documents

Non-Patent Document 1: Organic & Biomolecular Chemistry, 2008, Vol. 66, p. 1738 to 1742

SUMMARY OF THE INVENTION

Problems to be Solved by the Invention

As described above, there have been reported charge-transporting substances serving as wet process materials, which substances are indolocarbazole derivatives in which the two nitrogen atoms forming the indolocarbazole ring are substituted with an aryl group or another group (see, for example, Patent Documents 1 to 3). However, there has never been found an indolocarbazole derivative for use in a wet process in which neither of the two nitrogen atoms is substituted. Notably, although Non-Patent Document 1 discloses the synthesis of such an indolocarbazole compound, the document fails to disclose or suggest use of the synthesized indolocarbazole compounds as, for example, charge-transporting thin films (hole injection layer, hole transportation layer, etc.) of an organic EL element.

The present invention has been conceived in view of the foregoing. Thus, an object of the present invention is to provide a charge-transporting varnish comprising, as a charge-transporting substance, an indolocarbazole derivative in which neither of the two nitrogen atoms forming an indolocarbazole ring is substituted. Another object is to provide a charge-transporting thin film from the varnish. Still another object is to provide a method for producing the thin film. Yet another object is to provide an organic EL element having the thin film. Yet another object is to provide a method for producing the EL element.

Means for Solving the Problems

In one mode of the present invention to attain the aforementioned objects, there is provided a charge-transporting varnish, characterized by comprising a charge-transporting substance formed of an indolocarbazole represented by the following formula (1):

[F1]

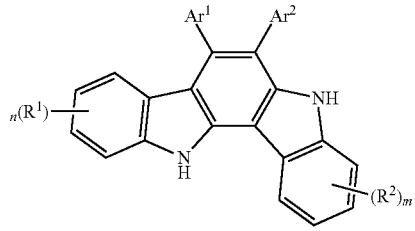

(1)

(wherein each of $Ar^1$ and $Ar^2$ independently represents a C6 to C20 aryl group optionally substituted by $Z^1$ or a C2 to C20 heteroaryl group optionally substituted by $Z^1$; each of $R^1$ and $R^2$ independently represents a halogen atom, a nitro group, a cyano group, an amino group, a dimethylamino group, a hydroxyl group, a C1 to C20 alkoxy group, a C1 to C20 alkyl group optionally substituted by $Z^2$, a C2 to C20 alkenyl group optionally substituted by $Z^2$, or a C2 to C20 alkynyl group optionally substituted by $Z^2$; $Z^1$ represents a halogen atom, a nitro group, a cyano group, an amino group, a dimethylamino group, a hydroxyl group, a C1 to C20 alkoxy group, a C1 to C20 alkyl group optionally substituted by $Z^2$, a C2 to C20 alkenyl group optionally substituted by $Z^2$, or a C2 to C20 alkynyl group optionally substituted by $Z^2$; $Z^2$ represents a halogen atom, a nitro group, a cyano group, an amino group, a dimethylamino group, a hydroxyl group, or a C1 to C20 alkoxy group; n represents the number of group(s) $R^1$; m represents the number of group(s) $R^2$; and each of n and m is independently an integer of 0 to 4), a dopant substance, and an organic solvent.

Preferably, the dopant substance contains at least one of an arylsulfonic acid compound and a heteropolyacid compound.

In another mode of the present invention to attain the aforementioned objects, there is provided a charge-transporting thin film, characterized by being formed of a charge-transporting varnish as recited above.

In still another mode of the present invention to attain the aforementioned objects, there is provided a method for producing a charge-transporting thin film, characterized in that the method comprises a step of applying a charge-transporting varnish as recited above onto a substrate, and a step of evaporating the organic solvent.

In yet another mode of the present invention to attain the aforementioned objects, there is provided an organic electroluminescent element, characterized by comprising a charge-transporting thin film as recited above.

Preferably, the charge-transporting thin film is at least one of a hole injection layer and a hole transportation layer.

In yet another mode of the present invention to attain the aforementioned objects, there is provided a method for producing an organic electroluminescent element, characterized in that the method employs a charge-transporting thin film as described above.

Effects of the Invention

The charge-transporting varnish of the present invention contains a charge-transporting substance formed of an indolocarbazole derivative in which neither of the two nitrogen atoms forming an indolocarbazole ring is substituted, and a dopant substance. Thus, when the varnish is employed, a thin film having excellent charge transportability can be produced. In addition, according to the charge-transporting varnish of the present invention, a thin film having excellent charge transportability can be suitably produced, even in the case where various wet processes (e.g., spin coating and slit coating) which enable formation of a large-area film are employed. Therefore, the charge-transporting varnish of the present invention satisfactorily catches up with the recent development in the field of organic EL element.

BRIEF DESCRIPTION OF THE DRAWINGS

FIG. 3(C2)] illustrates the formula of a heteropolyacid compound having a Dawson-type chemical structure in which a heteroatom is positioned at the center of the molecule.

MODES FOR CARRYING OUT THE INVENTION

Figure 1:
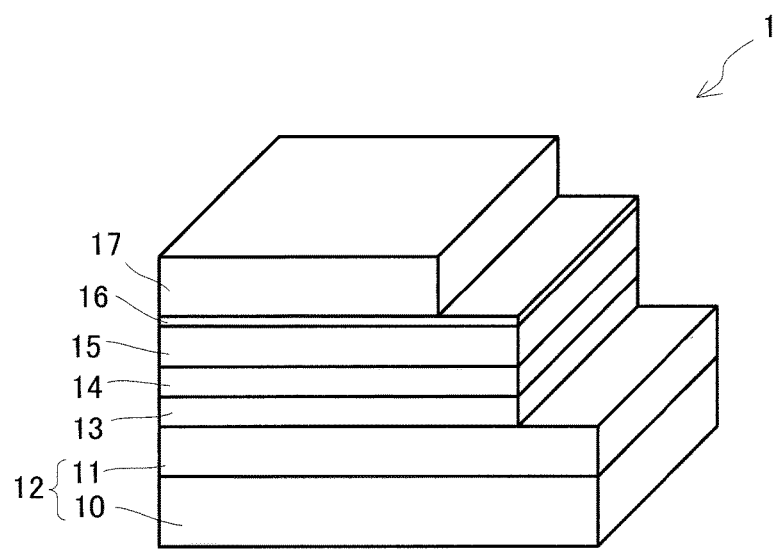
FIG. 1 A schematic view of an OLED element having a charge-transporting thin film according to the embodiment.

Hereinafter, an embodiment of the present invention will be described in detail. However, the embodiment of the invention is given merely for the purpose of illustration, and the embodiment may be arbitrarily modified within the scope of the present invention. Notably, the term "charge transportability" is equivalent to "electrical conductivity" or "hole transportability." The charge-transporting substance may per se have charge transportability or may exhibit charge transportability when used in combination with a dopant substance (an electron-accepting substance). Also, the charge-transporting varnish may per se have charge transportability, or a solid film produced from the varnish may have charge transportability.

The charge-transporting varnish of the embodiment contains a charge-transporting substance represented by formula (1), a dopant substance, and an organic solvent. More specifically, the charge-transporting varnish of the embodiment contains the charge-transporting substance mainly serving as a charge-transporting host material along with the dopant substance, which are dissolved in the organic solvent at such a total concentration that the varnish can be employed in a wet process. Among these ingredients, the charge-transporting substance is formed of an indolocarbazole derivative in which neither of the two nitrogen atoms an indolocarbazole ring is substituted. The present inventors have newly found that a charge-transporting thin film (e.g., a hole injection layer) of an organic EL element can be successfully formed through a wet process using a charge-transporting substance formed of such an indolocarbazole derivative.

[F2]

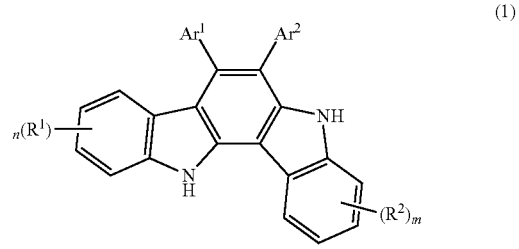

(1)

In formula (1), $Ar^1$ and $Ar^2$ independently represents a C6 to C20 aryl group optionally substituted by $Z^1$ or a C2 to C20 heteroaryl group optionally substituted by $Z^1$. Each of $R^1$ and $R^2$ independently represents a halogen atom, a nitro group, a cyano group, an amino group, a dimethylamino group, a hydroxyl group, a C1 to C20 alkoxy group, a C1 to C20 alkyl group optionally substituted by $Z^2$, a C2 to C20 alkenyl group optionally substituted by $Z^2$, or a C2 to C20 alkynyl group optionally substituted by $Z^2$. $Z^1$ represents a halogen atom, a nitro group, a cyano group, an amino group, a dimethylamino group, a hydroxyl group, a C1 to C20 alkoxy group, a C1 to C20 alkyl group optionally substituted by $Z^2$, a C2 to C20 alkenyl group optionally substituted by $Z^2$, or a C2 to C20 alkynyl group optionally substituted by $Z^2$. $Z^2$ represents a halogen atom, a nitro group, a cyano group, an amino group, a dimethylamino group, a hydroxyl group, or a C1 to C20 alkoxy group; n represents the number of group(s) $R^1$; m represents the number of group(s) $R^2$; and each of n and m is independently an integer of 0 to 4.

Examples of the C6 to C20 aryl group include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 4-biphenyl, and 4-terphenyl.

Examples of the C2 to C20 heteroaryl group include 2-thienyl, 3-thienyl, 2-furanyl, 3-furanyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl, and 4-pyridyl.

Examples of the halogen atom include fluorine, chlorine, bromine, and iodine. Examples of the C1 to C20 alkoxy group include methoxy, ethoxy, n-propoxy, isopropoxy, n-butoxy, isobutoxy, s-butoxy, t-butoxy, n-pentoxy, n-hexyloxy, n-heptyloxy, n-octyloxy, n-nonyloxy, and n-decyloxy.

The C1 to C20 alkyl group may be linear-chain, branched, or cyclic. Examples thereof include C1 to C20 linear-chain or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, and n-decyl; and C3 to C20 cycloalkyl groups such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl, and bicyclodecyl.

Examples of the C2 to C20 alkenyl group include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl, and n-1-eicosenyl.

Examples of the C2 to C20 alkynyl group include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl, and n-1-eicosynyl.

The aforementioned charge-transporting substance can be dissolved with a dopant substance in an organic solvent, to thereby provide a charge-transporting varnish which can suitably provide a charge-transporting thin film having excellent charge transportability, even in the case where various wet processes which enable formation of a large-area film are employed.

In one preferred mode, the charge-transporting substance employed in the embodiment attains a considerable solubility in organic solvent and a low molecular weight of the charge-transporting varnish. By use of such a charge-transporting substance, a charge-transporting varnish having excellent spreadability after application thereof can be produced. As a result, a large-area charge-transporting thin film having high flatness can be effectively attached to a transparent electrode (e.g., ITO or IZO) through a wet process such as spin coating.

Thus, in the above formula (1), at least one of n and m is preferably 0. More preferably, each of n and m is 0. As charge-transporting substances represented by formula (1), there may be used substances represented by the following formula (2):

[F3]

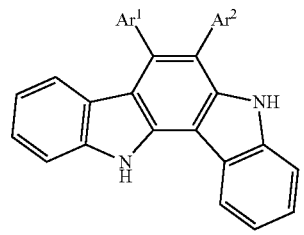

(2)

(wherein $Ar^1$ and $Ar^2$ have the same meanings as defined above).

From another aspect, in order to enhance the solubility of the charge-transporting substance in organic solvent, at least one of $Ar^1$ and $Ar^2$ in formula (1) or (2) is preferably an aryl group. More preferably, each of $Ar^1$ and $Ar^2$ is an aryl group. In the case where at least one of $Ar^1$ and $Ar^2$ in formula (1) is substituted by $Z^1$, $Z^1$ is preferably a halogen atom, more preferably a fluorine atom, in order to enhance charge transportability of the formed thin film.

Thus, examples of the charge-transporting substance employed in the embodiment include compounds represented by the following formulas (a-1) to (a-21). By use of a charge-transporting varnish produced by dissolving any of the above charge-transporting substances and a dopant substance in an organic solvent in the aforementioned manner, a charge-transporting thin film having excellent charge transportability can be produced. These charge-transporting substances have a low molecular weight and high solubility in organic solvent. Therefore, when the charge-transporting varnish containing such a charge-transporting substance is used, a large-area charge-transporting thin film having high flatness can be effectively produced through a wet process.

[F4]

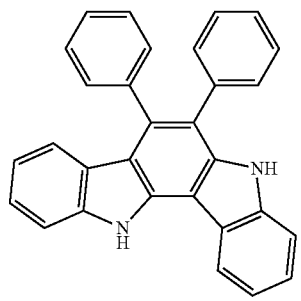

(a-1)

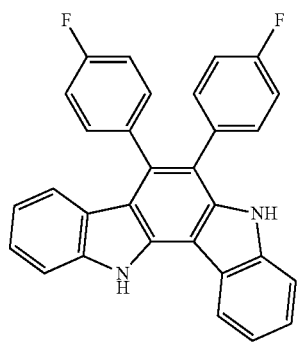

(a-2)

[F5]
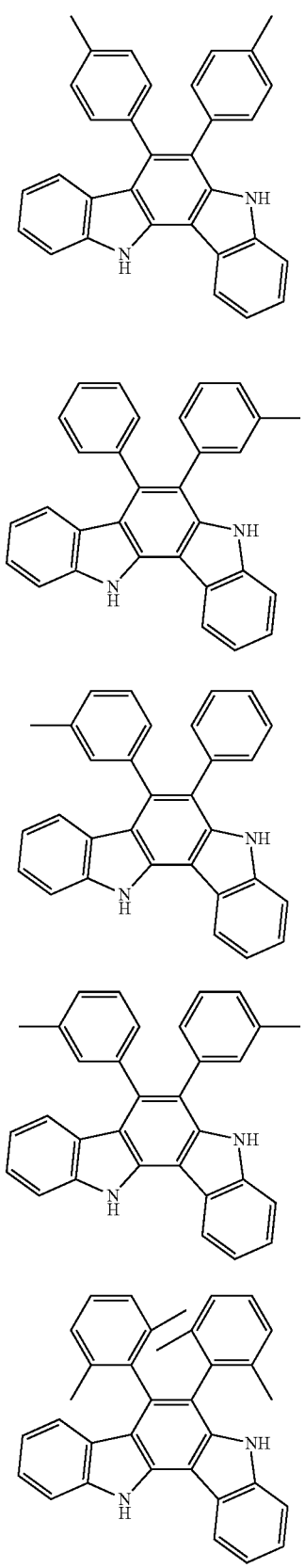
(a-3)
(a-4)
(a-5)
(a-6)
(a-7)
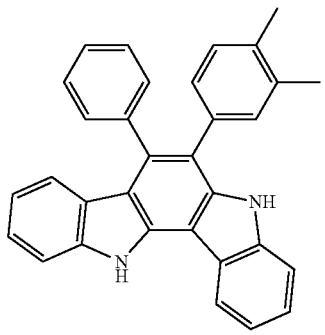
(a-8)
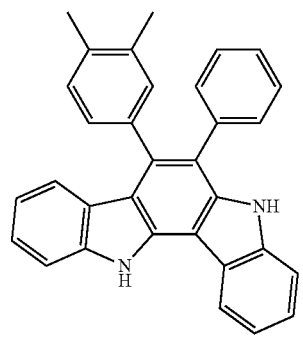
(a-9)
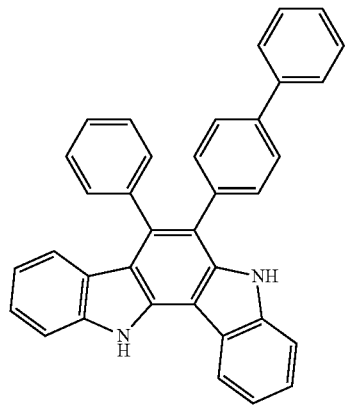
(a-10)
[F6]
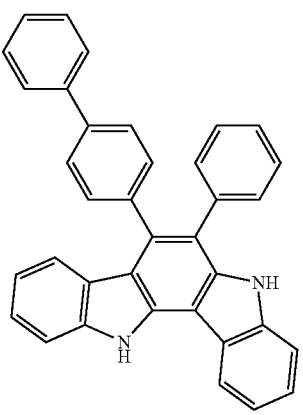
(a-11)

-continued
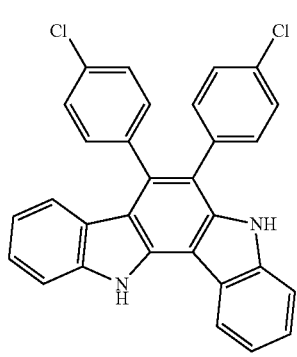
(a-12)
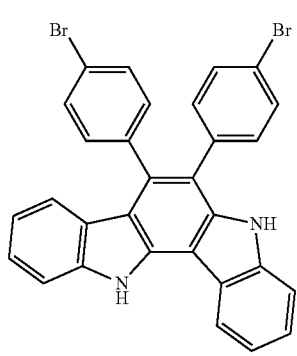
(a-13)
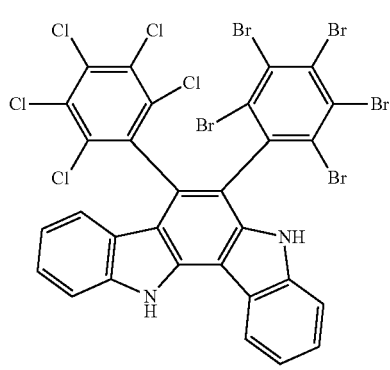
(a-14)
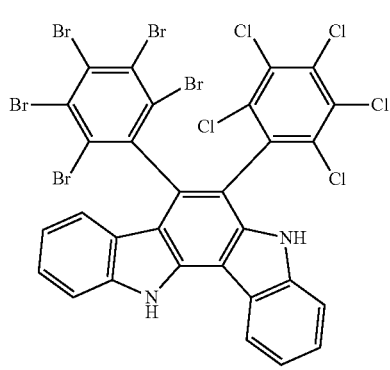
(a-15)
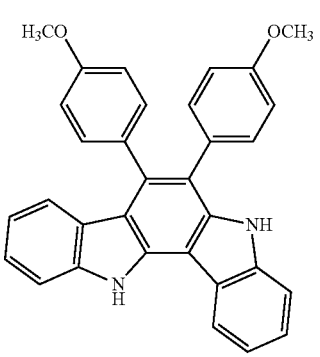
(a-16)
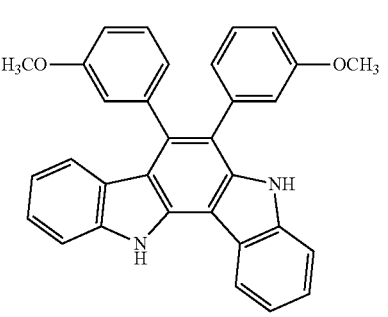
(a-17)
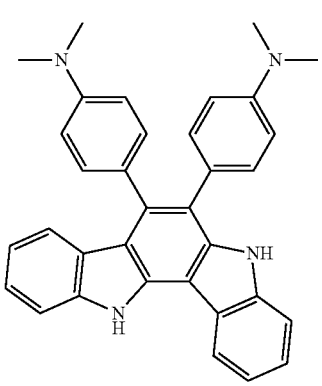
(a-18)
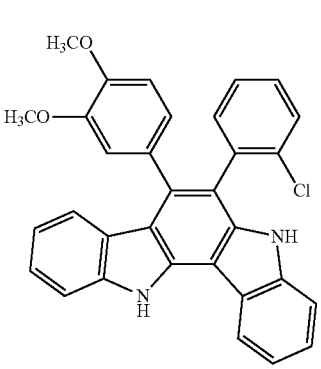
(a-19)

-continued

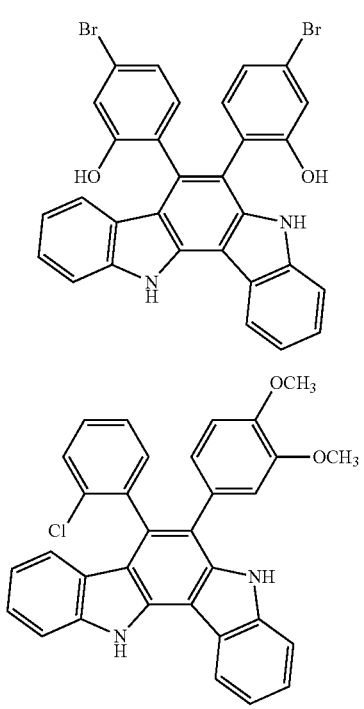

(a-20)

(a-21)

Notably, the charge-transporting substance of the embodiment may be synthesized through a method disclosed in Non-Patent Document 1; i.e., the following scheme:

[F7]

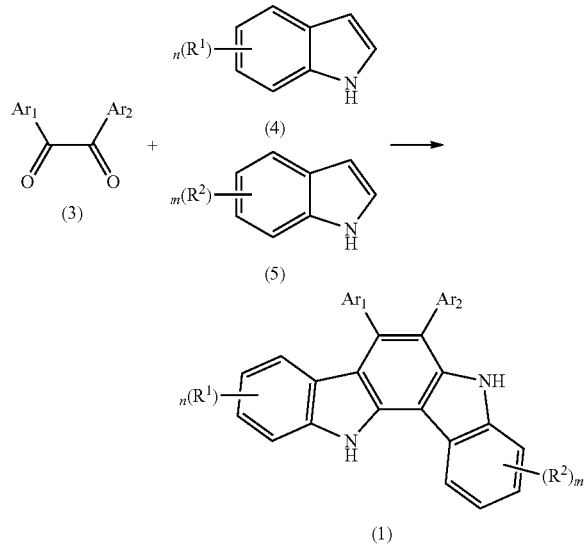

(wherein $Ar^1$ and $Ar^2$, n and m, and $R^1$ and $R^2$ have the same meanings as defined above).

In the above scheme, the compositional proportions among compounds represented by formulas (3) to (5) (formula (3): formulas (4) and (5)) may be appropriately tuned to about 1:2. Compounds represented by formulas (3) to (5) may be produced through a conventional method. However, commercial products thereof may also be used.

The aforementioned charge-transporting substance employed in the embodiment preferably has a molecular weight 2,000 or lower, more preferably 1,000 or lower, from the viewpoints of solubility in organic solvent and the like. Also, in the embodiment, such charge-transporting substances may be used singly or in combination of two or more species.

So long as the gist of the present invention is not changed, an additional charge-transporting substance may be used. Examples of the additional charge-transporting substance include an oligoaniline derivative disclosed in Japanese Patent Application Laid-Open (kokai) No. 2002-151272, an oligoaniline compound disclosed in WO 2004/105446 (pamphlet), a compound having a 1,4-dithiyne ring disclosed in WO 2005/043962 (pamphlet), an oligoaniline compound disclosed in WO 2008/032617 (pamphlet), an oligoaniline compound disclosed in WO 2008/032616 (pamphlet), and an aryldiamine compound disclosed in WO 2013/042623 (pamphlet).

Among them, an aniline derivative having a molecular weight of about 200 to about 4,000 is preferred as the additional charge-transporting substance.

Next, the dopant substance employed in the charge-transporting varnish of the embodiment will be described. No particular limitation is imposed on the dopant substance, and any dopant substance may be appropriately used, so long as the substance can be dissolved in an organic solvent, which is an ingredient of the charge-transporting varnish. From the viewpoint of enhancement in optical transmittance of the charge-transporting thin film, the dopant substance is preferably an arylsulfonic acid compound. In consideration of solubility in organic solvent, the molecular weight of the dopant substance is preferably 3,000 or lower, more preferably 2,000 or lower, still more preferably 1,000 or lower. Examples of the arylsulfonic acid compound suitably used as a dopant substance include compounds represented by the following formulas (6) and (7).

[F8]

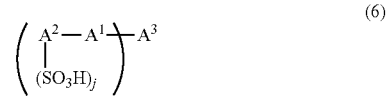

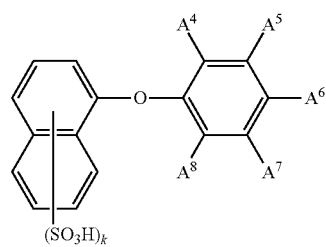

$A^1$ represents O or S and is preferably O.

$A^2$ represents a naphthalene ring or an anthracene ring and is preferably a naphthalene ring.

$A^3$ is a 2- to 4-valent perfluorobiphenyl group; 1 is a number (integer) of bonding(s) between A and $A^3$ satisfying: $2 \leq 1 \leq 4$. Preferably, $A^3$ is a divalent perfluorobiphenyl group, and 1 is 2.

The "j" is an integer of sulfonate group(s) bound to $A^2$ satisfying $1 \leq j \leq 4$. The number "j" is most preferably 2.

Each of $A^4$ to $A^8$ independently represents a hydrogen atom, a halogen atom, a cyano group, a C1 to C20 alkyl group, a C1 to C20 haloalkyl group, or a C2 to C20 haloalkenyl group. At least three of $A^4$ to $A^8$ are halogen atoms.

Examples of the C1 to C20 haloalkyl group include the above-described C1 to C20 alkyl groups in which at least one hydrogen atom is substituted by a halogen atom. Specific examples include trifluoromethyl, 2,2,2-trifluoroethyl, 1,1,2,2,2-pentafluoroethyl, 3,3,3-trifluoropropyl, 2,2,3,3,3-pentafluoropropyl, 1,1,2,2,3,3,3-heptafluoropropyl, 4,4,4-trifluorobutyl, 3,3,4,4,4-pentafluorobutyl, 2,2,3,3,4,4,4-heptafluorobutyl, and 1,1,2,2,3,3,4,4,4-nanofluorobutyl.

Examples of the C2 to C20 haloalkenyl group include the above-described C2 to C20 alkenyl groups in which at least one hydrogen atom is substituted by a halogen atom. Specific examples include perfluorovinyl, perfluoropropenyl (allyl), and perfluorobutenyl. Examples of the halogen atom and the C1 to C20 alkyl group include the same as described above. The halogen atom is preferably a fluorine atom.

to $A^8$ are halogen atoms. Still more preferably, each $A^4$ to $A^8$ is a fluorine atom, a fluorine atom, a cyano group, a C1 to C5 perfluoroalkyl group, or a C1 to C5 perfluoroalkenyl group, and $A^4$, $A^5$, and $A^8$ are fluorine atoms. Notably, the term "perfluoroalkyl group" refers to an alkyl group whose hydrogen atoms are completely substituted by fluorine atoms, and the term "perfluoroalkenyl group" refers to an alkenyl group whose hydrogen atoms are completely substituted by fluorine atoms.

The "k" is a number (integer) of sulfonic acid group(s) bound to the naphthalene ring satisfying 1≤k≤4 and is preferably 2 to 4, with 2 being most preferred. Specific examples of the arylsulfonic acid compound suitable for a dopant substance include the following.

[F9]

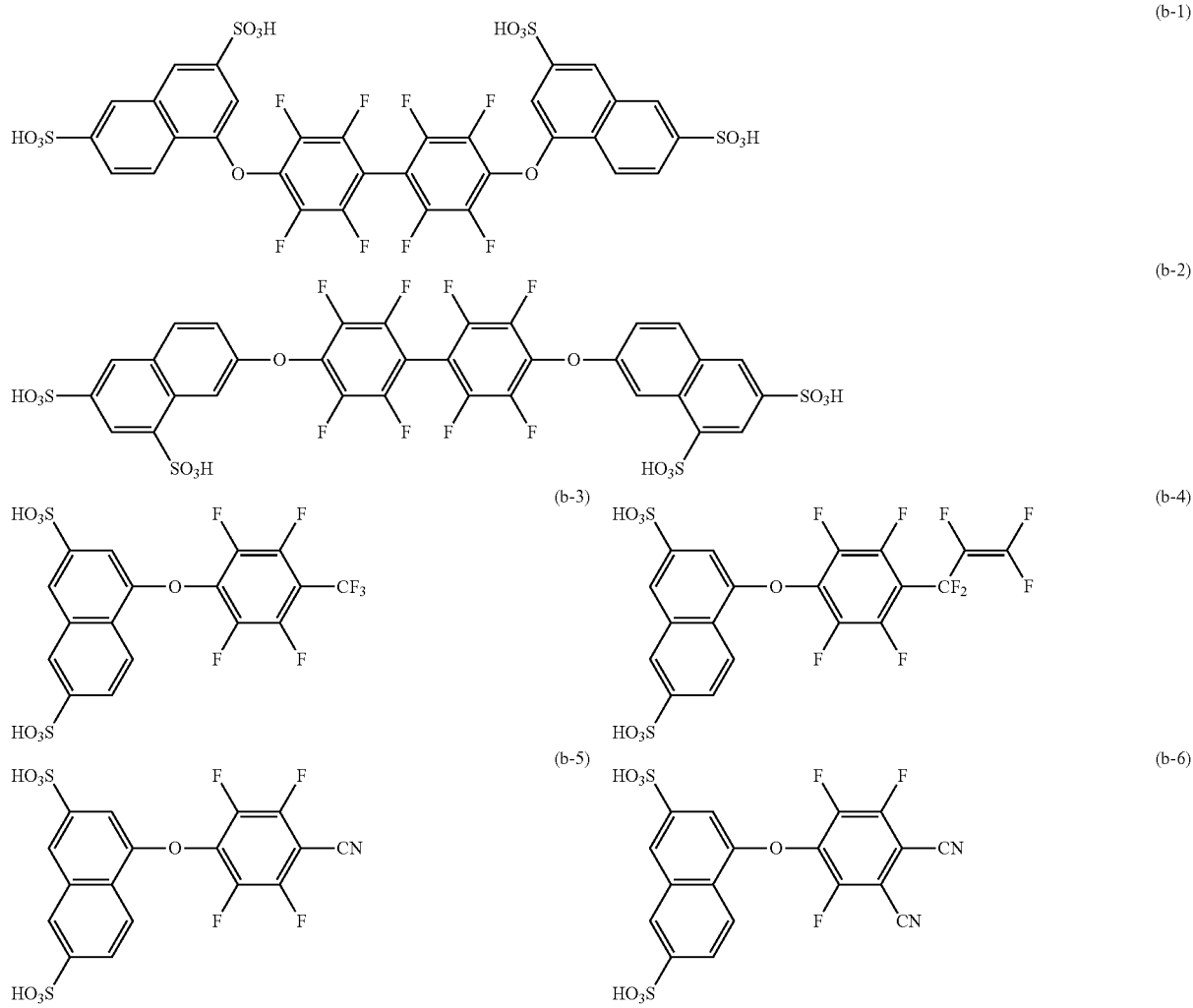

Preferably, each $A^4$ to $A^8$ is a hydrogen atom, a halogen atom, a cyano group, a C1 to C10 alkyl group, a C1 to C10 haloalkyl group, or a C2 to C10 haloalkenyl group, and at least three of $A^4$ to $A^8$ are fluorine atoms. More preferably, each $A^4$ to $A^8$ is a hydrogen atom, a fluorine atom, a cyano group, a C1 to C5 alkyl group, a C1 to C5 fluoroalkyl group, or a C2 to C5 fluoroalkenyl group, and at least three of $A^4$ However, the dopant substance is not limited to arylsulfonic acid compounds represented by formulas (b-1) to (b-6), and another arylsulfonic acid compound having a different structure may be used instead of or in combination with the above arylsulfonic acid compound. Furthermore, a dopant substance other than the arylsulfonic acid compound (i.e., another dopant substance) may be used instead of or in combination with the above arylsulfonic acid compound.

A suitable example of such a dopant substance other than the arylsulfonic acid compound is a heteropolyacid compound. When a heteropolyacid compound is employed as a dopant substance, there can be provided a charge-transporting thin film (e.g., a hole injection layer or a hole transportation layer) having excellent charge transportability and high hole accepting capacity from a transparent electrode (typically indium tin oxide (ITO) or indium zinc oxide (IZO)) as well as from a positive electrode formed of a metal (typically aluminum).

Figure 3:
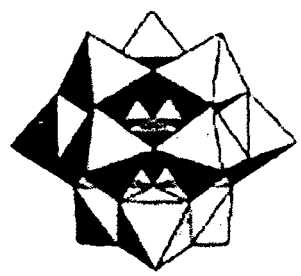
FIG. 3(C1) ] illustrates the formula of a heteropolyacid compound having a Keggin-type chemical structure in which a heteroatom is positioned at the center of the molecule.
Figure 3:
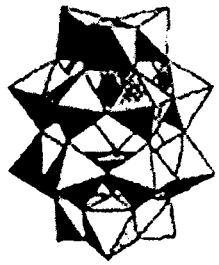

A heteropolyacid compound has a structure which includes a heteroatom at the center thereof and which is typically represented by the formula of FIG. 3(C1) (i.e., Keggin type) or the formula of FIG. 3(C2) (i.e., Dawson type). The heteropolyacid compound is formed from an isopolyacid; i.e., an oxoacid including vanadium (V), molybdenum (Mo), tungsten (W), or the like, condensed with another oxoacid including a heteroelement. Examples of typical heteroelements forming the oxoacid include silicon (Si), phosphorus (P), and arsenic (As).

Specific examples of the heteropolyacid compound include phosphomolybdic acid, silicomolybdic acid, phosphotungstic acid, silicotungstic acid, and phosphotungstomolybdic acid. These heteropolyacid compounds may be used singly or in combination of two or more species.

Notably, heteropolyacid compounds employable in the embodiment may be commercial products or may be synthesized through a known method.

Particularly when the dopant substance is formed of a heteropolyacid compound as a single component, the single heteropolyacid compound is preferably phosphotungustic acid or phosphomolybdic acid, with phosphotungustic acid being suitable. When the dopant substance is formed of two or more heteropolyacid compounds, one of these heteropolyacid compounds is preferably phosphotungustic acid or phosphomolybdic acid, with phosphotungustic acid being more preferred. Meanwhile, in a heteropolyacid compound, the number of constituent elements may be deviated (greater or smaller) from the stoichiometry represented by the corresponding general formula, demonstrated though a quantitative analysis (e.g., element analysis). However, such non-stoichiometric heteropolyacid compound may also be used in this embodiment, so long as the heteropolyacid compound is a commercially available product or has been appropriately synthesized through a known method.

The dopant substance employable in the embodiment is not limited to the aforementioned examples. So long as the gist of the present invention is not changed, another electron-accepting dopant substance may also be used. The dopant substance content of the charge-transporting varnish of the embodiment may be adjusted to about 1.0 to about 70.0 (ratio by mass) with respect to amount of charge-transporting substance as 1. The dopant substance content is preferably about 2.0 to about 60.0, more preferably about 2.5 to about 55.0, still more preferably about 2.5 to about 30.0, yet more preferably about 2.5 to about 20.0, further more preferably about 2.5 to about 10.0. The dopant substance contained in the charge-transporting varnish of the embodiment is not limited to a single species, and two or more dopant substances may be used in combination.

Next, the organic solvent contained in the charge-transporting varnish of the embodiment will be described. The organic solvent used in preparation of the charge-transporting varnish may be a high-solubility solvent (a rich solvent), which can suitably dissolve a charge-transporting substance and a dopant substance to such an extent that the charge-transporting varnish can be employed in a wet process. Examples of the high-solubility solvent include organic solvents such as N,N-dimethylformamide, N,N-dimethylacetamide, N-methylpyrrolidone, 1,3-dimethyl-2-imidazolidinone, diethylene glycol monomethyl ether, and propylene glycol monomethyl ether. These solvents may be used singly or in combination of two or more species. The amount of high-solubility solvent may be adjusted to 5 to 100 mass % with respect to the total amount of the solvent species used in the varnish.

Notably, the organic solvent employable in the embodiment is not limited to the aforementioned examples. A low-polar solvent having a polarity lower than the high-solubility solvent (a poor solvent) may be used instead of or in combination with the high-solubility solvent. Generally, such a low-polar solvent has low polarity of solvent molecules and poor solubility to a high-polarity compound.

However, some of low-polar solvents can enhance wettability to a substrate by virtue of enhanced viscosity, reduced surface tension, added volatility, etc. and, in some cases, may impart physical properties suitable for spraying or coating to the coating material when an applicator is employed, to thereby minimize corrosion to the applicator.

In the embodiment, when at least one high-viscosity organic solvent is added to the varnish, the viscosity of the varnish can be facilitated. Such high-viscosity organic solvent has a viscosity (25° C.) of 10 to 200 mPa·s, preferably 35 to 150 mPa·s, and a boiling point (atmospheric pressure) of 50 to 300° C., preferably 150 to 250° C. As a result, there can be provided a varnish which can form a charge-transporting thin film with high flatness at high reproducibility and which is satisfactorily adapted to the varnish application method. The ratio of added high-viscosity organic solvent to all the solvent species employed in the embodiment is preferably adjusted such that no solid deposition occurs. So long as no solid deposition occurs, the ratio is preferably 5 to 80 mass %. In addition, in order to enhance wettability to a substrate and to adjust surface tension, polarity, boiling point, etc. of the solvent, an additional solvent may be added to the solvent of the varnish at 1 to 90 mass % with respect to the amount of all the solvent species contained in the varnish, preferably 1 to 50 mass %.

The viscosity of the varnish of the embodiment, which is appropriately predetermined in accordance with the thickness and other parameters of the charge-transporting thin film and the solid content of the varnish, is generally 1 to 50 mPa·s at 25° C. The solid content of the charge-transporting varnish of the embodiment, which is appropriately predetermined in accordance with the viscosity, surface tension, etc. of the varnish, the thickness of the formed charge-transporting thin film, and other factors, is generally about 0.1 to about 10.0 mass %. From the viewpoint of enhancement in varnish coatability, the solid content is preferably 0.5 to 5.0 mass %, more preferably 1.0 to 3.0 mass %.

The aforementioned charge-transporting varnish is applied onto a substrate and fired, to thereby form a charge-transporting thin film on the substrate. No particular limitation is imposed on the method of applying the varnish, and examples of the application method include dipping, spin coating, transfer printing, roller coating, brush coating, ink-jet coating, and spraying. Preferably, the viscosity and surface tension of the varnish are adjusted in accordance with the application method.

In firing the charge-transporting varnish of the embodiment, the firing atmosphere is generally air. The firing temperature is appropriately set to fall within a range of about 100 to about 260° C., in consideration of uses of the produced charge-transporting thin film, charge transportability of the produced charge-transporting thin film, and other factors. In the case where the formed charge-transporting thin film is employed as a hole injection layer of an organic EL element, the firing temperature is preferably about 140 to about 2500C, more preferably about 145 to about 240° C. In firing, the temperature profile may include two or more steps, in order to provide higher uniformity in film formability and to suitably cause reaction on a substrate. Heating may be performed by means of, for example, an appropriate apparatus such as a hot plate or an oven.

No particular limitation is imposed on the thickness of the charge-transporting thin film. In the case where the charge-transporting thin film is employed as a hole injection layer of an organic EL element, the film thickness is preferably 5 to 200 nm. The film thickness may be modified through, for example, changing the solid content of the varnish or the amount of coating solution on a substrate during application of the solution.

In fabrication of a low-molecule organic EL element (hereinafter referred to as an OLED element) by use of the charge-transporting varnish of the embodiment, no particular limitation is imposed on the materials and fabrication method, and the following may be employed. The electrode substrate employed is preferably cleaned in advance with a liquid such as a detergent, alcohol, or pure water. In the case of a positive electrode substrate, the substrate is preferably subjected to surface treatment such as UV ozone treatment or oxygen-plasma treatment, just before use of the substrate. However, when the positive electrode material is mainly formed of an organic material, such surface treatment may be omitted.

FIG. 1 is a cross-section of the configuration of an OLED element having the charge-transporting thin film (e.g., a hole injection layer) of the embodiment. In one example, an OLED element 1 may be formed by sequentially stacking, on the surface of a glass substrate 10, an ITO substrate 12 (a positive electrode) having a patterned ITO layer 11, a hole injection layer 13, a hole transportation layer 14, a light-emitting layer 15, an electron injection layer 16, and an aluminum thin film 17 (a negative electrode). However, so long as the gist of the present invention is not limited, an additional layer may be further added thereto.

An example of the method of fabricating the OLED element 1 is as follows. Specifically, the charge-transporting varnish of the embodiment is applied onto the ITO substrate 12 serving as a positive electrode and then is fired. On the ITO substrate 12, the hole injection layer 13 is formed. The thus-obtained stacked structure is introduced into a vacuum vapor deposition apparatus, and the following layers (i.e., the hole transportation layer 14, the light-emitting layer 15, an optionally disposed electron transportation layer/hole-blacking layer (not illustrated), the electron injection layer 16, and the aluminum thin film 17 (an example of a negative electrode material)) are sequentially vapor-deposited, to thereby form the OLED element 1. Notably, if required, an optional electron-blocking layer may be disposed between the light-emitting layer 15 and the hole transportation layer 14.

Examples of the material of the positive electrode include a transparent electrode material (typically indium tin oxide (ITO) or indium zinc oxide (IZO)), and a positive electrode material formed of a metal (typically aluminum), an alloy thereof, etc. Preferably, the positive electrode is subjected in advance to planarization. Alternatively, a polythiophene derivative or a polyaniline derivative, having high charge transportability, may also be used.

The positive metal electrode may be formed of other metallic material. Examples include scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Examples of the material for forming the hole transportation layer 14 include (triphenylamine)dimer derivatives, [(triphenylamine)dimer] spirodimer,
N,N'-bis(naphthalen-1-yl)-N,N'-bis(phenyl)-benzidine (α-NPD),
N,N'-bis(naphthalen-2-yl)-N,N'-bis(phenyl)-benzidine,
N,N'-bis(3-methylphenyl)-N,N'-bis(phenyl)-benzidine,
N,N'-bis(3-methylphenyl)-N,N'-bis(phenyl)-9,9-spirobifluorene
N,N'-bis(naphthalen-1-yl)-N,N'-bis(phenyl)-9,9-spirobifluorene,
N,N'-bis(3-methylphenyl)-N,N'-bis(phenyl)-9,9-dimethylfluorene,
N,N'-bis(naphthalen-1-yl)-N,N'-bis(phenyl)-9,9-dimethylfluorene,
N,N'-bis(3-methylphenyl)-N,N'-bis(phenyl)-9,9-diphenylfluorene,
N,N'-bis(naphthalen-1-yl)-N,N'-bis(phenyl)-9,9-diphenylfluorene,
N,N'-bis(naphthalen-1-yl)-N,N'-bis(phenyl)-2,2'-dimethylbenzidine,
2,2',7,7'-tetrakis(N,N-diphenylamino)-9,9-spirobifluorene,
9,9-bis[4-(N,N-bis-biphenyl-4-yl-amino)phenyl]-9H-fluorene,
9,9-bis[4-(N,N-bis-naphthalen-2-yl-amino)phenyl]-9H-fluorene,
9,9-bis[4-(N-naphthalen-1-yl-N-phenylamino)-phenyl]-fluorene,
2,2',7,7'-tetrakis[N-naphthalenyl(phenyl)-amino]-9,9-spirobifluorene,
N,N'-bis(phenanthren-9-yl)-N,N'-bis(phenyl)-benzidine,
2,2'-bis[N,N-bis(biphenyl-4-yl)amino]-9,9-spirobifluorene,
2,2'-bis(N,N-diphenylamino)-9,9-spirobifluorene,
di-[4-(N,N-di(p-tolyl)amino)-phenyl]cyclohexane,
2,2',7,7'-tetra(N,N-di(p-tolyl))amino-9,9-spirobifluorene,
N,N,N',N'-tetra-naphthalen-2-yl-benzidine,
N,N,N',N'-tetra-(3-methylphenyl)-3,3'-dimethylbenzidine,
N,N'-di(naphthalenyl)-N,N'-di(naphthalen-2-yl)-benzidine,
N,N,N',N'-tetra(naphthalenyl)-benzidine,
N,N'-di(naphthalen-2-yl)-N,N'-diphenylbenzidine-1,4-diamine,
$N^1,N^4$-diphenyl-$N^1,N^4$-di(m-tolyl)benzene-1,4-diamine,
$N^2,N^2,N^6,N^6$,N-tetraphenylnaphthalene-2,6-diamine, tris(4-(quinolin-8-yl)phenyl)amine,
2,2'-bis(3-(N,N-di(p-tolyl)amino)phenyl)biphenyl, triarylamines such as
4,4',4''-tris[3-methylphenyl(phenyl)amino]triphenylamine (m-MTDATA) and
4,4',4''-tris[1-naphthyl(phenyl)amino]triphenylamine (1-TNATA); and oligothiophenes such as
5,5''-bis-{4-[bis(4-methylphenyl)amino]phenyl}-2,2': 5',2''-terthiophene (BMA-3T).

Examples of the material for forming the light-emitting layer 15 include tris(8-quinolinolato)aluminum(III) (Alq$_3$), bis(8-quinolinolato) zinc (II) (Znq$_2$), bis(2-methyl-8-quinolinolato) (p-phenylphenolato)aluminum(III) (BAlq), 4,4'-bis(2,2-diphenylvinyl)biphenyl,
9,10-di(naphthalen-2-yl)anthracene,
2-t-butyl-9,10-di(naphthalen-2-yl)anthracene,
2,7-bis[9,9-di(4-methylphenyl)-fluoren-2-yl]-9,9-di(4-methylphenyl)fluorene,
2-methyl-9,10-bis(naphthalen-2-yl)anthracene,
2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)-fluoren-2-yl]-9,9-di(4-methylphenyl)fluorene,
2,2'-dipyrenyl-9,9-spirobifluorene,
1,3,5-tris(pyren-1-yl)benzene,
9,9-bis[4-(pyrenyl)phenyl]-9H-fluorene,
2,2'-bi(9,10-diphenylanthracene),
2,7-dipyrenyl-9,9-spirobifluorene, 1,4-di(pyren-1-yl)benzene,
1,3-di(pyren-1-yl)benzene, 6,13-di(biphenyl-4-yl)pentacene,
3,9-di(naphthalen-2-yl)perylene,
3,10-di(naphthalen-2-yl)perylene,
tris[4-(pyrenyl)-phenyl]amine,
10,10'-di(biphenyl-4-yl)-9,9'-bianthracene,
N,N'-di(naphthalen-1-yl)-N,N'-diphenyl-[1,1':4',1":4",1"'-quaterphenyl]-4,4"'-diamine,
4,4'-di[10-(naphthalen-1-yl)anthracen-9-yl]biphenyl,
dibenzo{[f,f']-4,4',7,7'-tetraphenyl}diindeno[1,2,3-cd:1',2',3'-lm]perylene,
1-(7-(9,9'-bianthracen-10-yl)-9,9-dimethyl-9H-fluoren-2-yl)pyrene,
1-(7-(9,9'-bianthracen-10-yl)-9,9-dihexyl-9H-fluoren-2-yl)pyrene,
1,3-bis(carbazol-9-yl)benzene),
1,3,5-tris(carbazol-9-yl)benzene,
4,4',4"-tris(carbazol-9-yl)triphenylamine,
4,4'-bis(carbazol-9-yl)biphenyl,
4,4'-bis(carbazol-9-yl)-2,2'-dimethylbiphenyl,
2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene,
9,9-bis[4-(carbazol-9-yl)-phenyl]fluorene,
2,7-bis(carbazol-9-yl)-9,9-spirobifluorene,
1,4-bis(triphenylsilyl)benzene,
1,3-bis(triphenylsilyl)benzene,
bis(4-N,N-diethylamino-2-methylphenyl)-4-methylphenylmethane,
2,7-bis(carbazol-9-yl)-9,9-dioctylfluorene,
4,4'-di(triphenylsilyl)-p-terphenyl,
4,4'-di(triphenylsilyl)biphenyl,
9-(4-t-butylphenyl)-3,6-bis(triphenylsilyl)-9H-carbazol,
9-(4-t-butylphenyl)-3,6-ditrityl-9H-carbazol,
9-(4-t-butylphenyl)-3,6-bis(9-(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl)-9H-fluorene-2-amine,
3,5-bis(3-(9H-carbazol-9-yl)phenyl)pyridine,
9,9-spirobifluoren-2-yl-diphenyl-phosphine oxide,
9,9'-(5-(triphenylsilyl)-1,3-phenylene)bis(9H-carbazole)
3-(2,7-bis(diphenylphosphoryl)-9-phenyl-9H-fluoren-9-yl)enyl-9H-carbazole,
4,4,8,8,12,12-hexa(p-tolyl)-4H-8H-12H-12C-azadibenzo[cd,mn]pyrene, 4,7-di(9H-carbazol-9-yl)-1,10-phenanthroline,
2,2'-bis(4-(carbazol-9-yl)phenyl)biphenyl,
2,8-bis(diphenylphosphoryl)dibenzo[b,d]thiophene,
bis(2-methylphenyl)diphenylsilane,
bis(3,5-di(9H-carbazol-9-yl)phenyl]diphenylsilane,
3,6-bis(carbazol-9-yl)-9-(2-ethyl-hexyl)-9H-carbazol,
3-(diphenylphosphoryl)-9-(4-(diphenylphosphoryl)phenyl)-9H-carbazole, and 3,6-bis[(3,5-diphenyl)phenyl]-9-phenylcarbazole. Alternatively, the light-emitting layer 15 may be formed through co-vapor deposition with a light-emitting dopant.

Examples of the light-emitting dopant include
3-(2-benzothiazolyl)-7-(diethylamino)coumarin,
2,3,6,7-tetrahydro-1,1,7,7-tetramethyl-1H,5H,11H-10-(2-benzothiazoyl) quinolidino[9,9a,1gh]coumarin, quinacridone,
N,N'-dimethyl-quinacridone, tris(2-phenylpyridine)iridium (Ir(ppy)$_3$), bis(2-phenylpyridine) (acetylacetonato) iridium (Ir(ppy)$_2$(acac)), tris[2-(p-tolyl)pyridine]iridium (Ir(mppy)$_3$), 9,10-bis[N,N-di(p-tolyl)amino]anthracene,
9,10-bis[phenyl(m-tolyl)amino]anthracene,
bis[2-(2-hydroxyphenyl)benzothiazolato]zinc,
$N^{10},N^{10},N^{10'},N^{10'}$-tetra(p-tolyl)-9,9'-bianthracene-10,10'-diamine,
$N^{10},N^{10},N^{10'},N^{10'}$-tetraphenyl-9,9'-bianthracene-10,10'-diamine,
$N^{10},N^{10'}$-diphenyl-$N^{10'},N^{10'}$-dinaphthalenyl-9,9'-bianthracene-10,10'-diamine,
4,4'-bis(9-ethyl-3-carbazovinylene)-1,1'-biphenyl, perylene,
2,5,8,11-tetra-t-butylperylene,
1,4-bis[2-(3-N-ethylcarbazolyl)vinyl]benzene,
4,4'-bis[4-(di-p-tolylamino)styryl]biphenyl,
4-(di-p-tolylamino)-4'-[(di-p-tolylamino)styryl]stilbene,
bis(3,5-difluoro-2-(2-pyridyl)phenyl-(2-carboxypyridyl) iridium,
4,4'-bis[4-(diphenylamino)styryl]biphenyl,
bis(2,4-difluorophenylpyridinato)tetrakis(1-pyrazolyl)boratoiridium,
N,N'-bis(naphthalen-2-yl)-N,N'-bis(phenyl)-tris(9,9-dimethylfluorenylene),
2,7-bis{2-[phenyl(m-tolyl)amino]-9,9-dimethyl-fluoren-7-yl}-9,9-dimethyl-fluorene,
N-(4-((E)-2-(6((E)-4-(diphenylamino)styryl)naphthalen-2-yl)vinyl)phenyl)-N-phenylbenzeneamine,
fac-tris(1-phenyl-3-methylbenzimidazolin-2-ylidene-C, C$^{2'}$) iridium,
mer-tris(1-phenyl-3-methylbenzimidazolin-2-ylidene-C, C$^{2'}$) iridium, 2,7-bis[4-(diphenylamino)styryl]-9,9-spirobifluorene,
6-methyl-2-(4-(9-(4-(6-methylbenzo[d]thiazol-2-yl)phenyl)anthracen-10-yl)phenyl)benzo[d]thiazole,
1,4-di[4-(N,N-diphenyl)amino]styrylbenzene,
1,4-bis(4-(9H-carbazol-9-yl)styryl)benzene,
(E)-6-(4-(diphenylamino)styryl)-N,N-diphenylnaphthalen-2-amine,
bis(2,4-difluorophenylpyridinato) (5-(pyridin-2-yl)-1H-tetrazolato)iridium,
bis(3-trifluoromethyl-5-(2-pyridyl)pyrazole) ((2,4-difluorobenzyl)diphenylphosphinato)iridium,
bis(3-trifluoromethyl-5-(2-pyridyl)pyrazolato) (benzyldiphenyl phosphinato)iridium,
bis(1-(2,4-difluorobenzyl)-3-methylbenzimidazolium) (3-(trifluoromethyl)-5-(2-pyridyl)-1,2,4-triazolato)iridium,
bis(3-trifluoromethyl-5-(2-pyridyl)pyrazolato) (4',6'-difluoro phenylpyridinato)iridium,
bis(4',6'-difluorophenylpyridinato) (3,5-bis(trifluoromethyl)-2-(2'-pyridyl)pyrrolato)iridium,
bis(4',6'-difluorophenylpyridinato) (3-(trifluoromethyl)-5-(2-pyridyl)-1,2,4-triazolato)iridium, (Z)-6-mesityl-N-(6-mesitylquinolin-2(1H)-ylidene)quinoline-2-amine-BF$_2$,
(E)-2-(2-(4-(dimethylamino)styryl)-6-methyl-4H-pyran-4-yliden e)malononitrile,
4-(dicyanomethylene)-2-methyl-6-durolidyl-9-enyl-4H-pyrane,
4-(dicyanomethylene)-2-methyl-6-(1,1,7,7-tetramethyl-durolidyl-9-enyl)-4H-pyrane,
4-(dicyanomethylene)-2-t-butyl-6-(1,1,7,7-tetramethyldurolidin-4-yl-vinyl)-4H-pyrane,
tris(dibenzoylmethane)phenanthrolineeuropium,
5,6,11,12-tetraphenylnaphthacene,
bis(2-benzo[b]thiophen-2-yl-pyridine) (acetylacetonato) iridium,
tris(1-phenylisoquinoline)iridium,
bis(1-phenylisoquinoline) (acetylacetonato)iridium,
bis[1-(9,9-dimethyl-9H-fluoren-2-yl)-isoquinoline](acetylacetonato)iridium,
bis[2-(9,9-dimethyl-9H-fluorene-2-yl)quinoline](acetylacetonato)iridium, tris[4,4'-di-t-butyl-(2,2')-bipyridine]ruthenium bis(hexafluorophosphate), tris(2-phenylquinoline)iridium,
bis(2-phenylquinoline) (acetylacetonato)iridium,
2,8-di-t-butyl-5,11-bis(4-t-butylphenyl)-6,12-diphenyltetracene, bis(2-phenylbenzothiazolato) (acetylacetonato)iridium,
5,10,15,20-tetraphenyltetrabenzoporphylineplatinum,
bis(3-trifluoromethyl-5-(2-pyridine)-pyrazolate)dimethylphenylphosphinosmium,
bis(3-(trifluoromethyl)-5-(4-t-butylpyridyl)-1,2,4-triazolato)diphenylmethylphosphineosmium,
bis(3-(trifluoromethyl)-5-(2-pyridyl)-1,2,4-triazole)dimethylphenylphosphineosmium,
bis(3-(trifluoromethyl)-5-(4-t-butylpyridyl)-1,2,4-triazolato)dimethylphenylphosphineosmium,
bis[2-(4-n-hexylphenyl)quinoline](acetylacetonato) iridium,
tris[2-(4-n-hexylphenyl) quinoline]iridium,
tris[2-phenyl-4-methylquinoline)]iridium,
bis(2-phenylquinoline) (2-(3-methylphenyl)pyridinato) iridium,
bis(2-(9,9-diethyl-fluoren-2-yl)-1-phenyl-1H-benzo[d]imidazolato) (acetylacetonato)iridium,
bis(2-phenylpyridine) (3-(pyridin-2-yl)-2H-couromen-2-onato) iridium,
bis(2-phenylquinoline) (2,2,6,6-tetramethylheptan-3,5-dionato)iridium,
bis(phenylisoquinoline) (2,2,6,6-tetramethylheptan-3,5-dionato)iridium, iridiumbis(4-phenylthieno[3,2-c]pyridinato-N, C$^{2'}$) acetylacetonato,
(E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)malononitrile,
bis(3-trifluoromethyl-5-(1-isoquinolyl)pyrazolato) (methyldiphenylphosphine)ruthenium,
bis[(4-n-hexylphenyl)isoquinoline](acetylacetonato) iridium, platinum octaethylporphyin,
bis(2-methyldibenzo[f,h]quinoxaline) (acetylacetonato) iridium, and tris[(4-n-hexylphenyl) isoquinoline]iridium.

Examples of the material for forming the electron transportation layer/hole-blocking layer include
8-hydroxyquinolinolate-lithium,
2,2',2"-(1,3,5-benzintolyl)-tris(l-phenyl-1-H-benzimidazole), 2-(4-biphenyl)5-(4-t-butylphenyl)-1,3,4-oxadiazole,
2,9-dimethyl-4,7-diphenyl-1,10-phenanthroline,
4,7-diphenyl-1,10-phenanthroline,
bis(2-methyl-8-quinolilato)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-t-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dime thylfluorene,
1,3-bis[2-(4-t-butylphenyl)-1,3,4-oxadizao-5-yl]benzene,
tris(2,4,6-trimethyl-3-(pyridin-3-yl)phenyl)borane,
1-methyl-2-(4-(naphthalen-2-yl)phenyl)-1H-imidazo[4,5f][1,10]phenanthroline,
2-(naphthalen-2-yl)-4,7-diphenyl-1,10-phenanthroline, phenyl-dipyrenylphosphine oxide,
3,3',5,5'-tetra[(m-pyridyl)-phen-3-yl]biphenyl,
1,3,5-tris[(3-pyridyl)-phen-3-yl]benzene,
4,4'-bis(4,6-diphenyl-1,3,5-triazin-2-yl)biphenyl,
1,3-bis[3,5-di(pyridin-3-yl)phenyl]benzene,
bis(10-hydroxybenzo[h]quinolinato)beryllium,
diphenylbis(4-(pyridin-3-yl)phenyl)silane, and
3,5-di(pyren-1-yl)pyridine.

Examples of the material for forming the electron injection layer 16 include lithium oxide (Li$_2$O), magnesium oxide (MgO), alumina (Al$_2$O$_3$), lithium fluoride (LiF), sodium fluoride (NaF), magnesium fluoride (MgF$_2$), cesium fluoride (CsF), strontium fluoride (SrF$_2$), molybdenum trioxide (MoO$_3$), aluminum, Li(acac), lithium acetate, and lithium benzoate.

Examples of the negative electrode material include aluminum, magnesium-silver alloy, aluminum-lithium alloy, lithium, sodium, potassium, and cesium. Examples of the material for forming the electron-blocking layer include tris(phenylpyrazole)iridium.

Figure 2:
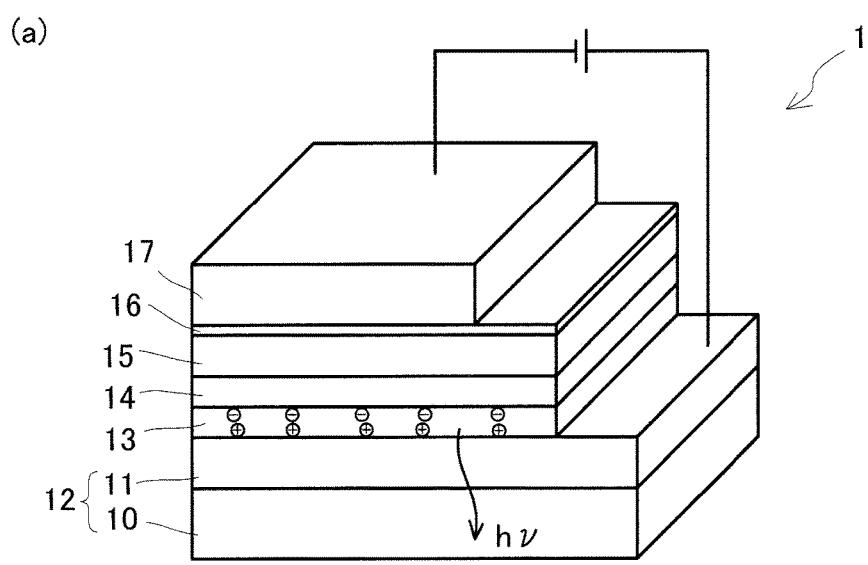
FIG. 2 Schematic views of an OLED element having a charge-transporting thin film according to the embodiment.
Figure 2:
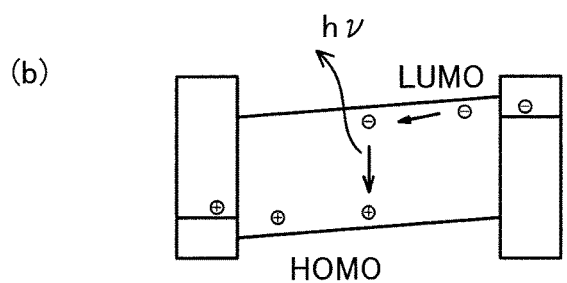

As shown in FIGS. 2(a) and 2(b), when a voltage is applied to the ITO substrate 12 (positive electrode) and the aluminum thin film 17 (negative electrode) of the OLED element 1, HOMO and LUMO are provided with internal gradient.

Thus, holes are injected to HOMO by moving from the ITO substrate 12 side to the light-emitting layer 15 side, and electrons are injected to LUMO by moving from the aluminum thin film 17 side to the light-emitting layer 15 side. As a result, holes and electrons are recombined in the light-emitting layer 15 (i.e., the energy of excited molecules is transferred from the electron transporting material to the dopant substance), whereby light is emitted to the outside of the OLED element 1 through the ITO substrate 12.

No particular limitation is imposed on the method for fabricating a polymer-type organic EL element (hereinafter referred to as a PLED element) employing the charge-transporting varnish of the embodiment. An example of the fabrication method is as follows. Specifically, in the aforementioned fabrication of the OLED element 1, vacuum vapor deposition of the hole transportation layer 14, the light-emitting layer 15, the electron transportation layer (not illustrated), and the electron injection layer 16 is omitted. Instead, a hole-transporting polymer layer and a light-emitting polymer layer are sequentially formed, to thereby fabricate a PLED element having a charge-transporting thin film formed from the charge-transporting varnish of the embodiment. More specifically, the charge-transporting varnish of the embodiment is applied onto the positive electrode substrate, and a hole injection layer is formed according to the aforementioned technique. On the hole-injection layer, a hole-transporting polymer layer and a light-emitting polymer layer are sequentially formed, and a negative electrode is formed through vapor deposition, to thereby fabricate a PLED element.

The same materials as employed in fabrication of the OLED element may be used as materials for producing the negative electrode and the positive electrode. Also, the same cleaning treatment and surface treatment may be performed. In one mode of forming the hole-transporting polymer layer and the light-emitting polymer layer, a hole-transporting polymer material or a light-emitting polymer material, or such a material to which a dopant substance has been added is dissolved or uniformly dispersed in a solvent.

The thus-obtained liquid is applied onto the hole-injecting polymer layer or the hole-transporting polymer layer, and firing is performed, to thereby form a layer of interest.

Examples of the hole-transporting polymer material include
poly[(9,9-dihexylfluorenyl-2,7-diyl)-co-(N,N'-bis{p-butyl-phen yl}-1,4-diaminophenylene)],
poly[(9,9-dioctylfluorenyl-2,7-diyl)-co-(N,N'-bis{p-butyl-phen yl}-1,1'-biphenylene-4,4-diamine)],
poly[(9,9-bis{1'-penten-5'-yl}fluorenyl-2,7-diyl)-co-(N,N'-bi s{p-butylphenyl}-1,4-diaminophenylene)],
poly[N,N'-bis(4-butylphenyl)-N,N'-bis(phenyl)-benzidine] endo-capped with polysilsesquinoxane, and
poly[(9,9-dioctylfluorenyl-2,7-diyl)-co-(4,4'-(N-(p-butyl-phen yl))diphenylamine)].

Examples of the light-emitting polymer material include polyfluorene derivatives such as poly(9,9-dialkylfluorene) (PDAF); polyphenylenevinylene derivatives such as poly(2-methoxy-5-(2'-ethylhexoxy)-1,4-phenylenevinylene) (MEH-PPV); polythiophene derivatives such as poly(3-alkylthiophene) (PAT); and polyvinylcarbazol (PVCz).

Examples of the solvent include toluene, xylene, and chloroform. Examples of the method of dissolution or uniform dispersion include stirring, stirring under heating, and dispersing with ultrasonication. No particular limitation is imposed on the liquid application technique, and examples thereof include ink jetting, spraying, dipping, spin coating, transfer printing, roller coating, and brush coating. The coating process is preferably performed under an inert gas such as nitrogen or argon. Examples of the firing method include firing under inert gas or in vacuum by means of an oven or a hot plate.

EXAMPLES

The present invention will next be described in more detail by way of the Examples and Comparative Examples, which should not be construed as limiting the invention thereto.

The apparatuses employed in Examples are as follows.
Wash substrate: substrate washing apparatus (reduced pressure plasma type) (product of Choshu Industry)
Application of varnish: Spin-coater MS-A100 (product of Mikasa Co., Ltd.)
Film thickness measurement: microfigure measurement instrument "Surfcorder ET-4000" (product of Kosaka Laboratory Ltd.)
Transmittance measurement: UV-Visible absorption spectrometer UV-3100PC (product of Shimadzu Corporation)
Fabrication of organic EL element: multifunction vapor deposition apparatus system C-E2L1G1-N(product of Choshu Industry)

Measurement of luminance, etc. of organic EL element: I-V-L measurement system (product of Tech-World)

Synthesis Example 1

A compound represented by the following formula (a-1) (hereinafter the compound is abbreviated as A1) and a compound represented by the following formula (a-2) (hereinafter the compound is abbreviated as A2) were synthesized through a method disclosed in the above-mentioned Non-Patent Document 1.

[F11]

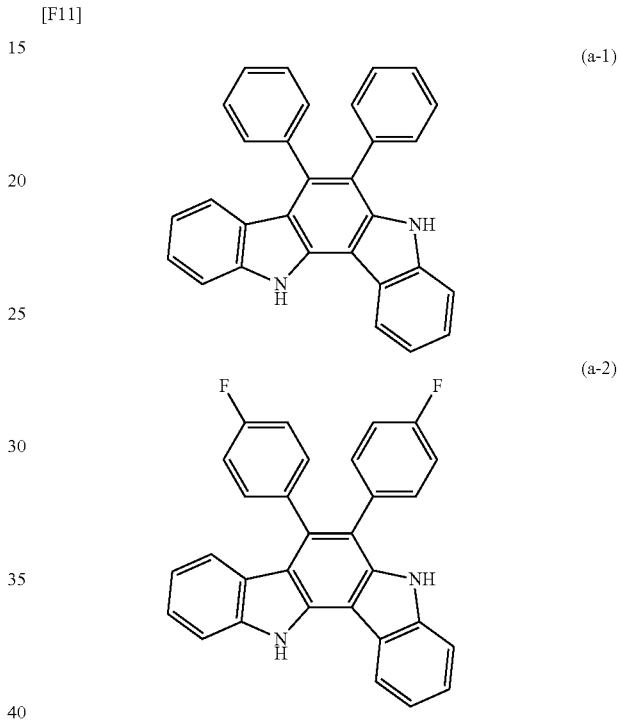

<Synthesis of A1>
Indole (7.00 g), benzil (5.01 g), p-toluenesulfonic acid monohydrate (0.92 g), and toluene (55 mL) were sequentially added to a reaction container, and the atmosphere of the reaction system was substituted to nitrogen. Then, the solution was stirred for 8 hours under heat reflux conditions. The thus-treated solution was cooled to room temperature and filtered. The residue was purified through column chromatography, and fractions each containing a target compound were collected. The solvent of the combined fractions was removed through distillation, and the residue was dried. The thus-obtained powder was recrystallized from 1,4-dioxane (120 mL), and the crystals obtained through filtration were dried, to thereby yield 4.95 g of 6,7-diphenyl-5,12-dihydroindolo[3,2-a]carbazole (yield: 51%).

1H NMR (300 MHz, THF-d8) δ [ppm]: 10.8 (s, 1H), 9.91 (s, 1H), 8.47 (d, J=7.7 Hz, 1H), 7.51 (d, J=7.7 Hz, 1H), 7.48 (d, J=7.7 Hz, 1H), 7.08-7.35 (m, 13H), 6.74-6.80 (m, 2H).

<Synthesis of A2>
Indole (1.17 g), 1,2-bis(4-fluorophenyl)ethane-1,2-dione (0.98 g), p-toluenesulfonic acid monohydrate (0.15 g), and toluene (10 mL) were sequentially added to a reaction container, and the atmosphere of the reaction system was substituted to nitrogen. Then, the solution was stirred for 7 hours under heat reflux conditions. The thus-treated solution was cooled to room temperature and filtered. The residue was washed with a mixture of toluene, tetrahydrofuran, and ethanol and dried, to thereby yield 0.46 g of 6,7-bis(4-fluorophenyl)-5,12-dihydroindolo[3,2-a]carbazole (yield: 26%).

$^1$H NMR (300 MHz, DMSO-d6) δ [ppm]: 11.9 (s, 1H), 10.8 (s, 1H), 8.72 (d, J=7.7 Hz, 1H), 7.64 (d, J=8.3 Hz, 1H), 7.57 (d, J=8.3 Hz, 1H), 7.11-7.43 (m, 11H), 6.87 (t, J=7.7 Hz, 1H), 6.60 (d, J=7.7 Hz, 1H).

<Preparation of Varnish>

Example 1-1

To a mixture of A1 (0.073 g, 0.178 mmol) and an arylsulfonic acid compound represented by the following formula (b-1) (hereinafter abbreviated as B1) (0.080 g, 0.089 mmol), a good solvent 1,3-dimethyl-2-imidazolidinone (hereinafter abbreviated as DMI) (2.5 g) was added under nitrogen, to thereby form a solution. To the solution, cyclohexanol (3.75 g) and propylene glycol (1.25 g) were added, and the contents were sufficiently stirred, to thereby yield a clear yellow solution. The clear yellow solution was filtered through a PTFE filter (pore size: 0.2 μm), to thereby yield a clear yellow charge-transporting varnish (solid content: 2.0 mass %). B1 was synthesized in accordance with WO 2006/025342.

[F12]

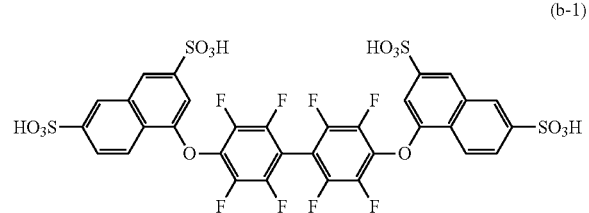

(b-1)

Example 1-2

The procedure of Example 1-1 was repeated, except that a mixture of A1 (0.061 g, 0.136 mmol) and B1 (0.092 g, 0.102 mmol) was used, to thereby yield a clear yellow charge-transporting varnish (solid content: 2.0 mass %).

Example 1-3

The procedure of Example 1-1 was repeated, except that a mixture of A1 (0.048 g, 0.117 mmol) and B1 (0.105 g, 0.117 mmol) was used, to thereby yield a clear yellow charge-transporting varnish (solid content: 2.0 mass %).

Example 1-4

To a mixture of A1 (0.048 g, 0.117 mmol) and B1 (0.105 g, 0.117 mmol), DMI (2.5 g) was added under nitrogen, to thereby form a solution. To the solution, cyclohexanol (3.75 g) and propylene glycol (1.25 g) were added, and the contents were sufficiently stirred. Thereafter, a 1:2 (by mass) mixture (0.015 g) of trimethoxy(3,3,3-trifluoropropyl)silane and tri(methoxyphenyl)silane was further added thereto, and the contents were sufficiently stirred, to thereby yield a clear yellow solution. The clear yellow solution was filtered through a PTFE filter (pore size: 0.2 μm), to thereby yield a clear yellow charge-transporting varnish (solid content: 2.0 mass %).

Example 1-5

The procedure of Example 1-1 was repeated, except that a mixture of A1 (0.046 g, 0.114 mmol) and phosphotungstic acid (product of Kanto Kagaku) (0.186 g) was used, to thereby yield a clear yellow charge-transporting varnish (solid content: 3.0 mass %).

Example 1-6

To a mixture of A2 (0.043 g, 0.097 mmol) and phosphotungstic acid (0.173 g), DMI (5 g) was added under nitrogen, to thereby form a solution. To the solution, cyclohexanol (1.0 g) and propylene glycol (1.0 g) were added, and the contents were sufficiently stirred, to thereby yield a clear yellow solution. The clear yellow solution was filtered through a PTFE filter (pore size: 0.2 μm), to thereby yield a clear yellow charge-transporting varnish (solid content: 3.0 mass %).

<Production of Charge-transporting Thin Film (Quartz Substrate) and Assessment of Transparency of the Charge-transporting Thin Film>

Examples 2-1 to 2-6

Each of the thus-obtained varnishes (Examples 1-1 to 1-6) was applied onto a quartz substrate by means of a spin coater, and the applied varnish was dried in air at 50° C. for 5 minutes, followed by firing at 230° C. for 15 minutes, whereby a uniform thin film having a thickness of 30 nm was formed on the quartz substrate. Notably, impurity matter on the surface of the quartz substrate was removed by means of a plasma cleaner (150 W, 30 seconds), and the thus-cleaned quartz substrate was used.

The transmittance of each of the produced charge-transporting thin films (Examples 2-1 to 2-6) was measured.

The transmittance was determined by scanning a wavelength range of 400 to 800 nm (i.e., visible light region). Table 1 shows the average transmittance (400 to 800 nm) measurements.

TABLE 1

| | Transmittance (%) |
|---|---|
| Example 2-1 | 96 |
| Example 2-2 | 96 |
| Example 2-3 | 95 |
| Example 2-4 | 97 |
| Example 2-5 | 92 |
| Example 2-6 | 93 |

As is clear from Table 1, the charge-transporting thin films (Examples 2-1 to 2-6) were found to exhibit high light transmittance in the visible light region.

<Fabrication of OLED Element, and Characteristic Assessment of the Element (Electric and Luminance Characteristics)>

Example 3-1

An OLED element 1 shown in FIG. 1 was fabricated through the following procedure. Specifically, an ITO substrate 12 was used as a substrate. The substrate was formed of a glass substrate 10 (25 mm×25 mm×0.7 t) on which a patterned ITO 11 film (thickness 150 nm) was disposed. Impurity matter on the surface of the ITO substrate 12 was removed by means of an $O_2$ plasma cleaner (150 W, 30 seconds), and the thus-cleaned substrate was used.

Firstly, the varnish of Example 1-1 was applied onto the ITO substrate 12 by means of a spin coater, and dried at 50° C. for 5 minutes, followed by firing at 230° C. for 15 minutes, to thereby form a uniform charge-transporting thin film (i.e., a hole injection layer 13) having a thickness of 30 nm on the ITO substrate 12.

On the charge-transporting thin film-attached ITO substrate 12, α-NPD (hole transportation layer 14), $Alq_3$ (light-emitting layer 15), lithium fluoride (LiF, electron injection layer 16), and aluminum thin film 17 were sequentially stacked by means of a vapor deposition apparatus, to thereby fabricate the OLED element 1. The thicknesses of the layers were adjusted to 30 nm, 40 nm, 0.5 nm, and 100 nm, respectively. The employed vacuum degree was $1.0 \times 10^{-5}$ Pa, and the deposition rate was adjusted to 0.02 nm/sec in the case of LiF, and 0.2 nm/sec for other materials.

Notably, in order to prevent deterioration in characteristics due to oxygen, water, etc. contained in air, the OLED element 1 was sealed with sealing substrates for correctly assessing the characteristics of the element.

Sealing was performed in the following manner.

In a nitrogen atmosphere (oxygen concentration: <5 ppm, dew point: −80° C. or lower), the OLED element 1 was bonded in a sandwich manner to sealing substrates by use of an adhesive. In this procedure, a moisturizer HD-071010W-40 (product of Dynic Corporation) was added to sealing substrates with the OLED element. As an adhesive, MORESCO Moisture Cut WB90US(P) (product of MORESCO) was used. The attached sealing substrates were irradiated with UV light (wavelength: 365 nm, dose: 6,000 mJ/cm$^2$). Then, the substrates were annealed at 80° C. for 1 hour, to thereby cure the adhesive.

Examples 3-2 to 3-6

The procedure of Example 3-1 was repeated, except that any of the varnishes produced in Examples 1-2 to 1-6 was used, to thereby fabricate OLED elements.

The current density and luminance of each of the produced OLED elements (Examples 3-1 to 3-6) were determined.

Table 2 shows measurements of current density and luminance at a driving voltage of 5 V. The emission face area of each element was 2 mm×2 mm.

TABLE 2

|  | Alq element (5 V) | |
| --- | --- | --- |
|  | Current density [mA/cm$^2$] | Luminance [cd/m$^2$] |
| Example 3-1 | 50 | 1,610 |
| Example 3-2 | 70 | 1,910 |
| Example 3-3 | 70 | 1,800 |
| Example 3-4 | 210 | 5,430 |
| Example 3-5 | 90 | 2,200 |
| Example 3-6 | 90 | 2,200 |

As is clear from Table 2, the OLED elements of Examples 3-1 to 3-6 were found to attain satisfactory luminance within a practical voltage range (i.e., to satisfactorily emit light). Thus, when the charge-transporting thin film produced from the charge-transporting varnish of the embodiment is employed as a hole injection layer, an organic EL element exhibiting excellent luminance characteristics can be provided.

DESCRIPTION OF REFERENCE NUMERALS 1 low-molecule organic EL element (OLED element), 10 glass substrate, 11 ITO, 12 ITO substrate (positive electrode), 13 hole injection layer (charge-transporting thin film), 14 hole transportation layer, 15 light-emitting layer, 16 electron injection layer, 17 aluminum thin film (negative electrode)

The invention claimed is:

1. A charge-transporting varnish, characterized by comprising a charge-transporting substance formed of an indolocarbazole represented by formula (1):

[F1]

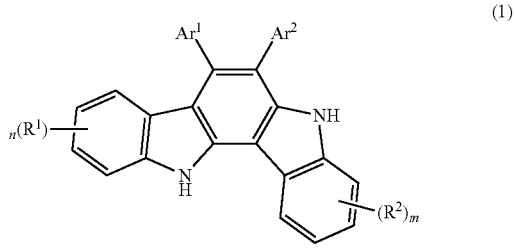

(1)

(wherein $Ar^1$ and $Ar^2$ independently represents a C6 to C20 aryl group optionally substituted by $Z^1$ or a C2 to C20 heteroaryl group optionally substituted by $Z^1$; Each of $R^1$ and $R^2$ independently represents a halogen atom, a nitro group, a cyano group, an amino group, a dimethylamino group, a hydroxyl group, a C1 to C20 alkoxy group, a C1 to C20 alkyl group optionally substituted by $Z^2$, a C2 to C20 alkenyl group optionally substituted by $Z^2$, or a C2 to C20 alkynyl group optionally substituted by $Z^2$; $Z^1$ represents a halogen atom, a nitro group, a cyano group, an amino group, a dimethylamino group, a hydroxyl group, a C1 to C20 alkoxy group, a C1 to C20 alkyl group optionally substituted by $Z^2$, a C2 to C20 alkenyl group optionally substituted by $Z^2$, or a C2 to C20 alkynyl group optionally substituted by $Z^2$; $Z^2$ represents a halogen atom, a nitro group, a cyano group, an amino group, a dimethylamino group, a hydroxyl group, or a C1 to C20 alkoxy group; n represents the number of group(s) $R^1$; m represents the number of group(s) $R^2$; and each of n and m is independently an integer of 0 to 4), a dopant substance, and an organic solvent.

2. A charge-transporting varnish according to claim 1, wherein the dopant substance contains at least one of an arylsulfonic acid compound and a heteropolyacid compound.

3. A charge-transporting thin film, characterized by being formed of a charge-transporting varnish as recited in claim 1.

4. A method for producing a charge-transporting thin film, characterized in that the method comprises a step of applying a charge-transporting varnish as recited in claim 1 onto a substrate, and a step of evaporating the organic solvent.

5. An organic electroluminescent element, characterized by comprising a charge-transporting thin film as recited in claim 3.

6. An organic electroluminescent element according to claim 5, wherein the charge-transporting thin film is at least one of a hole injection layer and a hole transportation layer.

7. A method for producing an organic electroluminescent element, characterized in that the method employs a charge-transporting thin film as recited in claim 3.

\* \* \* \* \*